US012582778B2

(12) United States Patent
Koshimoto et al.

(10) Patent No.: US 12,582,778 B2
(45) Date of Patent: Mar. 24, 2026

(54) SURFACE COATING LAYER FORMATION METHOD AND GASKET MANUFACTURING METHOD

(71) Applicant: KOKOKU INTECH CO., LTD, Tokyo (JP)

(72) Inventors: Akira Koshimoto, Saitama (JP); Kazuhiro Takahara, Saitama (JP)

(73) Assignee: KOKOKU INTECH CO., LTD, Tokyo (JP)

( * ) Notice: Subject to any disclaimer, the term of this patent is extended or adjusted under 35 U.S.C. 154(b) by 27 days.

(21) Appl. No.: 18/854,058

(22) PCT Filed: Mar. 28, 2023

(86) PCT No.: PCT/JP2023/012541
§ 371 (c)(1),
(2) Date: Oct. 3, 2024

(87) PCT Pub. No.: WO2023/195389
PCT Pub. Date: Oct. 12, 2023

(65) Prior Publication Data
US 2025/0065052 A1    Feb. 27, 2025

(30) Foreign Application Priority Data
Apr. 8, 2022    (JP) ................................. 2022-064355

(51) Int. Cl.
A61M 5/315        (2006.01)
(52) U.S. Cl.
CPC ..... A61M 5/31513 (2013.01); A61M 2207/10 (2013.01)
(58) Field of Classification Search
CPC ...................... A61M 5/31513; A61M 2207/10
See application file for complete search history.

(56) References Cited

U.S. PATENT DOCUMENTS 5,110,621 A     5/1992  Sudo et al.
6,296,907 B1 *  10/2001  Viksne ................. C09D 183/04
                                                427/393.5

(Continued)

FOREIGN PATENT DOCUMENTS

JP              162170 A1      3/1989
JP       H07126417 A1      5/1995

(Continued)

OTHER PUBLICATIONS

International Search Report and Written Opinion for International Application No. PCT/JP2023/012541, mailing date of Jul. 4, 2023.

*Primary Examiner* — Nathan T Leong
(74) *Attorney, Agent, or Firm* — Fresh IP PLC; Clifford D. Hyra; Aubrey Y. Chen

(57)        ABSTRACT

Disclosed herein is a surface coating layer formation method and a gasket manufacturing method capable of reducing the falling off of insoluble fine particles into a liquid medicine while preventing leakage of the liquid medicine and maintaining stable slidability. A material of a surface layer has a composition in which silicon-based rubber particles are contained in a silicon-based solution, and a surface coating layer formation method includes an application step of applying the material to a surface of a base material so as to have a predetermined coating thickness; a drying step of drying a sliding member after the application at a first temperature for a first time period; a baking step of baking the sliding member after the drying at a second temperature for a second time period; and a cleaning step of extraction-cleaning the sliding member after the baking at a third temperature for a third time period.

8 Claims, 9 Drawing Sheets

(56)         References Cited

U.S. PATENT DOCUMENTS

2007/0299402 A1    12/2007  Ishii et al.
2011/0313363 A1    12/2011  D'Souza et al.
2022/0267572 A1*    8/2022  Iwasaki .................. C08K 13/02

FOREIGN PATENT DOCUMENTS

JP          2006167110  A      6/2006
JP            2008287  A1      1/2008
WO          2021065739  A1      4/2021

* cited by examiner (a)

| | STUDY NUMBER | | | ① | ② | ③ | ⑤ | ⑥ | ⑦ | ⑧ |
|---|---|---|---|---|---|---|---|---|---|---|
| | COATING FORMULATION | | | FORMULATION 1 | FORMULATION 2 | FORMULATION 3 | FORMULATION 5 | FORMULATION 6 | FORMULATION 1 | FORMULATION 3 |
| SAMPLE PREPARATION CONDITION | CLEANING STEP | HIGH-PRESSURE EXTRACTION CLEANING | 125°C × 45min | ○ | ○ | ○ | ○ | ○ | | |
| COATING COMPONENT | FLEXIBILITY-IMPARTING COMPONENT | | | SILICON-BASED MATERIAL | SILICON-BASED MATERIAL | SILICON-BASED MATERIAL | URETHANE-BASED MATERIAL | URETHANE-BASED MATERIAL | SILICON-BASED MATERIAL | SILICON-BASED MATERIAL |
| | SLIDABILITY-IMPARTING COMPONENT | | | SILICON-BASED MATERIAL | -- | FLUORINE-BASED MATERIAL | SILICON-BASED MATERIAL | FLUORINE-BASED MATERIAL | SILICON-BASED MATERIAL | FLUORINE-BASED MATERIAL |
| TEST CONTENT | SLIDING RESISTANCE VALUE | [N] | | 3.9 | 6.8 | 5.8 | INDISPERSIBLE | 21.1 | 3.7 | -- |
| | LEAKAGE TEST | [-] | | NO LEAKAGE | NO LEAKAGE | NO LEAKAGE | | - | NO LEAKAGE | - |
| | INSOLUBLE FINE PARTICLE TEST | [PIECES/3 mL] | 5 μm OR MORE | 7 | 8 | 28 | | 27 | 63 | 60 |
| | | [PIECES/3 mL] | 10 μm OR MORE | 5 | 5 | 8 | | 21 | 50 | 65 |
| | | [PIECES/3 mL] | 25 μm OR MORE | 0 | 0 | 0 | | 0 | 15 | 21 |

FIG. 5A

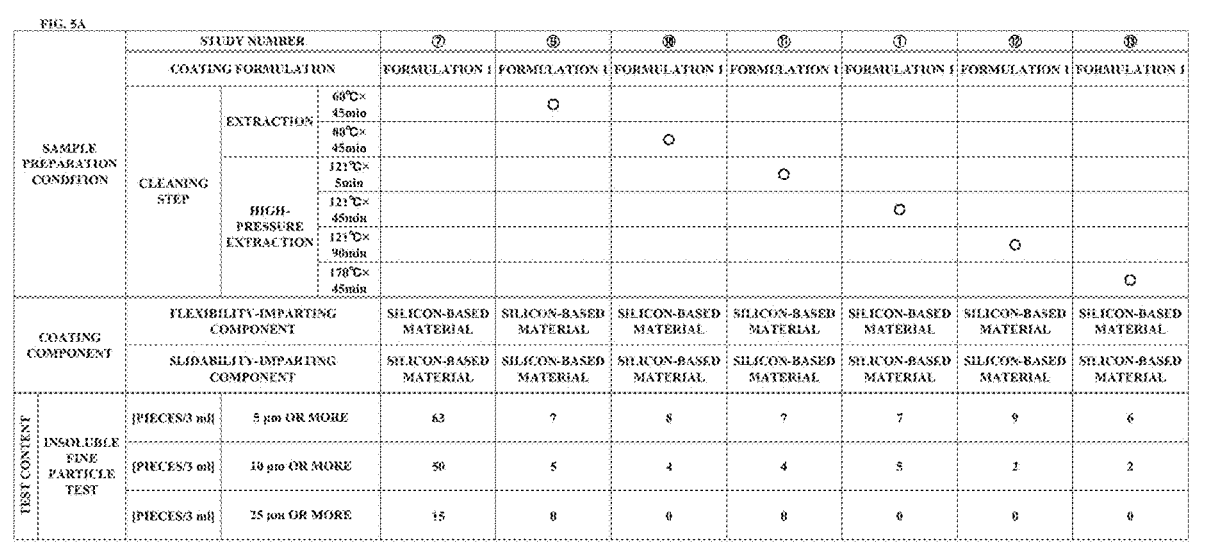

| | | | STUDY NUMBER | ㉗ | ㉘ | ㉙ | ㉚ | ㉛ | ㉜ | ㉝ |
|---|---|---|---|---|---|---|---|---|---|---|
| | | | COATING FORMULATION | FORMULATION 1 | FORMULATION 1 | FORMULATION 1 | FORMULATION 1 | FORMULATION 1 | FORMULATION 1 | FORMULATION 1 |
| SAMPLE PREPARATION CONDITION | CLEANING STEP | EXTRACTION | 60°C × 45min | | O | | | | | |
| | | | 80°C × 45min | | | O | | | | |
| | | HIGH-PRESSURE EXTRACTION | 121°C × 5min | | | | O | | | |
| | | | 121°C × 45min | | | | | O | | |
| | | | 121°C × 90min | | | | | | O | |
| | | | 178°C × 45min | | | | | | | O |
| COATING COMPONENT | FLEXIBILITY-IMPARTING COMPONENT | | | SILICON-BASED MATERIAL | SILICON-BASED MATERIAL | SILICON-BASED MATERIAL | SILICON-BASED MATERIAL | SILICON-BASED MATERIAL | SILICON-BASED MATERIAL | SILICON-BASED MATERIAL |
| | SLIDABILITY-IMPARTING COMPONENT | | | SILICON-BASED MATERIAL | SILICON-BASED MATERIAL | SILICON-BASED MATERIAL | SILICON-BASED MATERIAL | SILICON-BASED MATERIAL | SILICON-BASED MATERIAL | SILICON-BASED MATERIAL |
| TEST CONTENT | INSOLUBLE FINE PARTICLE TEST | [PIECES/3 ml] | 5 µm OR MORE | 62 | 7 | 8 | 7 | 7 | 9 | 6 |
| | | [PIECES/3 ml] | 10 µm OR MORE | 50 | 5 | 4 | 4 | 5 | 1 | 2 |
| | | [PIECES/3 ml] | 25 µm OR MORE | 15 | 0 | 0 | 0 | 0 | 0 | 0 |

FIG.6A

| | | | STUDY NUMBER | ① | ⑭ | ⑮ | ⑯ | ⑰ |
|---|---|---|---|---|---|---|---|---|
| SAMPLE PREPARATION CONDITION | | | COATING FORMULATION | FORMULATION 1 | FORMULATION 1 | FORMULATION 1 | FORMULATION 1 | FORMULATION 1 |
| | CLEANING STEP | HIGH-PRESSURE EXTRACTION CLEANING | 121°C × 45min | O | | | | O |
| | | SHAKING APPARATUS | | | O | | | |
| | | ULTRASONIC | | | | O | | O |
| | | SHAKER | | | | | O | |
| COATING COMPONENT | | FLEXIBILITY-IMPARTING COMPONENT | | SILICON-BASED MATERIAL | SILICON-BASED MATERIAL | SILICON-BASED MATERIAL | SILICON-BASED MATERIAL | SILICON-BASED MATERIAL |
| | | SLIDABILITY-IMPARTING COMPONENT | | SILICON-BASED MATERIAL | SILICON-BASED MATERIAL | SILICON-BASED MATERIAL | SILICON-BASED MATERIAL | SILICON-BASED MATERIAL |
| TEST CONTENT | SLIDING RESISTANCE VALUE | [N] | | 3.9 | 4.4 | 4.8 | 4.2 | 3.7 |
| | LEAKAGE TEST | [-] | | NO LEAKAGE | NO LEAKAGE | NO LEAKAGE | NO LEAKAGE | NO LEAKAGE |
| | INSOLUBLE FINE PARTICLE TEST | [PIECES/3 ml] | 5 μm OR MORE | 7 | 25 | 14 | 24 | 8 |
| | | [PIECES/3 ml] | 10 μm OR MORE | 5 | 13 | 6 | 13 | 5 |
| | | [PIECES/3 ml] | 25 μm OR MORE | 0 | 4 | 1 | 0 | 0 |

SURFACE COATING LAYER FORMATION METHOD AND GASKET MANUFACTURING METHOD

This application is a National Phase entry of International Application No. PCT/JP20223/012541 under § 371 and claims the benefit of Japanese Patent Application No. JP2022-064355, filed Apr. 8, 2022, which is hereby incorporated by reference in its entirety.

FIELD OF THE DISCLOSURE

The present disclosure relates to a surface coating layer formation method and a gasket manufacturing method.

BACKGROUND

Conventionally, a prefilled syringe filled with a liquid medicine in advance has been used. The prefilled syringe (hereinafter, referred to as a syringe) includes an outer barrel, a gasket, a plunger, and a cap. The gasket prevents leakage of the liquid medicine. In order to enhance slidability of the gasket, it has been proposed to increase slidability (namely, to reduce sliding resistance) of the gasket in the outer barrel, for example, by coating a surface of the gasket with a coating film composed of a flexibility-imparting component (for example, urethane resin) and a sliding component (for example, fluororesin) (for example, refer to Patent Document 1).

Patent Document 1: JP-A-2006-167111

SUMMARY

However, when the surface of the gasket is coated with solid fine particles or the like to enhance slidability as in the conventional art, there is a problem that the solid fine particles held in the coating film are separated therefrom and insoluble fine particles are mixed into the liquid medicine. For this reason, a surface coating layer formation method and a gasket manufacturing method that reduce the falling off of the insoluble fine particles into the liquid medicine while preventing leakage of the liquid medicine and maintaining stable slidability have been required.

The present disclosure has been made in view of the above-described circumstances, and an exemplary object of embodiments of the present invention is to provide a surface coating layer formation method and a gasket manufacturing method capable of reducing the falling off of insoluble fine particles into a liquid medicine while preventing leakage of the liquid medicine and maintaining stable slidability.

In order to solve the above-described problem, embodiments of the present invention have the following configurations.

(1) A surface coating layer formation method by which a surface coating layer for improving slidability is formed on a surface of a sliding member using rubber as a base material, a material of the surface coating layer having a composition in which silicon-based rubber particles are contained in a silicon-based solution, the method including: an application step of applying the material to a surface of the base material so as to have a predetermined coating thickness; a drying step of drying the sliding member after the application at a first temperature for a first time period; a baking step of baking the sliding member after the drying at a second temperature for a second time period; and a cleaning step of extraction-cleaning the sliding member after the baking at a third temperature for a third time period.

(2) A surface coating layer formation method by which a surface coating layer for improving slidability is formed on a surface of a gasket that is disposed at a tip portion of a plunger used in a syringe and that slides against an inner barrel wall of the syringe, a material of the surface coating layer having a composition in which silicon-based rubber particles are contained in a silicon-based solution, the method including: an application step of applying the material to the surface of the gasket so as to have a predetermined coating thickness; a drying step of drying the gasket after the application at a first temperature for a first time period; a baking step of baking the gasket after the drying at a second temperature for a second time period; and a cleaning step of extraction-cleaning the gasket after the baking at a third temperature for a third time period.

(3) A gasket manufacturing method by which a gasket that is disposed at a tip portion of a plunger used in a syringe and that slides against an inner barrel wall of the syringe, the gasket including a surface coating layer for improving slidability on a surface of a rubber base material, a material of the surface coating layer having a composition in which silicon-based rubber particles are contained in a silicon-based solution, the method including: an application step of applying the material to a surface of the base material so as to have a predetermined coating thickness; a drying step of drying the gasket after the application at a first temperature for a first time period; a baking step of baking the gasket after the drying at a second temperature for a second time period; and a cleaning step of extraction-cleaning the gasket after the baking at a third temperature for a third time period.

Further objects or other characteristics of embodiments of the present invention will become apparent by a preferred embodiment that will be described below with reference to the accompanying drawings.

According to embodiments of the present invention, it is possible to provide the surface coating layer formation method and the gasket manufacturing method capable of reducing the falling off of insoluble fine particles into the liquid medicine while preventing leakage of the liquid medicine and maintaining stable slidability.

BRIEF DESCRIPTION OF THE DRAWINGS

FIG. 4 is a view showing the results of Evaluation 1 of the embodiment, FIG. 4(a) is a table showing the results of Evaluation 1.

FIG. 5 is a view showing the results of Evaluation 2 of the embodiment, FIG. 5(a) is a table showing the results of Evaluation 2.

DETAILED DESCRIPTION

Hereinafter, an embodiment will be described with reference to the drawings. Here, a longitudinal direction of a syringe is a direction in which a plunger is pushed in, and is defined as an X direction. In addition, a direction in which the plunger is pushed in and a liquid medicine is released from a nozzle is defined as a positive (+) direction of the X direction.

EMBODIMENT

<Syringe>

Figure 1:
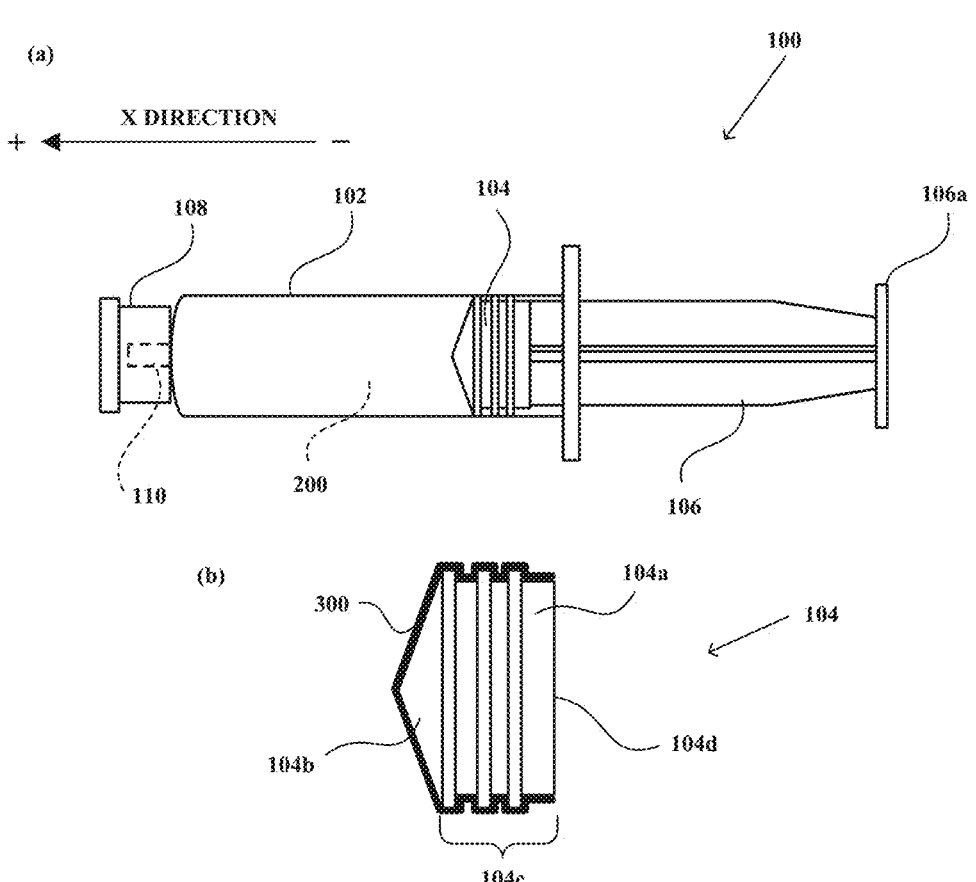
FIG. 1(a) is a schematic side view showing a configuration of a syringe.
FIG. 1(b) is a schematic side view showing a configuration of a gasket according to an embodiment.

A syringe of the present embodiment will be described. FIG. 1(*a*) is a schematic side view showing a configuration of the syringe according to the present embodiment, and also shows the X direction, the positive sign (+), and the negative sign (−). A syringe 100 includes an outer barrel 102, a gasket 104, a plunger 106, and a nozzle 110. A cap 108 and a liquid medicine 200 may be present.

The outer barrel 102 has, for example, a cylindrical shape with a circular cross section perpendicular to the longitudinal direction. The outer barrel 102 forms a space thereinside, which is filled with the liquid medicine 200 indicated by a dashed line, together with the gasket 104. The outer barrel 102 is made of, for example, glass, resin, or the like. For example, a lubricant or the like may be applied to an inner surface of the outer barrel 102 to enhance slidability against the gasket 104 (namely, to reduce sliding resistance) and to obtain high flow accuracy without causing a large disturbance in the discharge of the liquid medicine. As the lubricant, for example, silicone oil or the like may be used.

The gasket 104 is mounted on one end of the plunger 106, and slides in contact with the inner surface (inner barrel wall) of the outer barrel 102 when the plunger 106 is pushed in in the +X direction. A connecting portion between the gasket 104 and the plunger 106 has, for example, a recessed shape on a gasket 104 side and a protruding shape on a plunger 106 side, and a protruding portion of the plunger 106 is fitted to a recessed portion on the gasket 104 side. The configuration is such that for example, male screw threads are formed on the protruding portion of the plunger 106, for example, female screw grooves are formed on the recessed portion of the gasket 104, and the male screw threads and the female screw grooves are screwed to each other. The gasket 104 will be described later.

The gasket 104 is mounted on the one end (+ side) of the plunger 106 in the X direction, and a part of the plunger 106 is inserted into the outer barrel 102, together with the gasket 104. The plunger 106 includes a flange 106*a* at the other end (− side) in the X direction, a finger of a user being placed on the flange 106*a*. By pushing the flange 106*a* toward the + side in the X direction, the entirety of the plunger 106 is moved toward the + side in the X direction. The more the plunger 106 moves toward the +X side in the X direction, the greater extent the entry of the plunger 106 into the outer barrel 102 is. Incidentally, the syringe 100 is not limited to being directly operated by a user, and may be mounted and used in, for example, a device such as a syringe pump.

The other end (− side) of the nozzle 110 in the X direction is continuous with the space in the outer barrel 102, which is filled with the liquid medicine 200. One end (+ side) of the nozzle 110 in the X direction is open, and when the plunger 106 moves to the + side in the X direction, in a case where the outer barrel 102 is filled with the liquid medicine, the liquid medicine 200 is released from an opening of the nozzle 110.

In a prefilled syringe, the cap 108 seals the nozzle 110 such that the liquid medicine 200 does not leak from the nozzle 110 when it is not timing to release the liquid medicine 200 from inside of the syringe 100. The cap 108 may cover the nozzle 110 for the purpose of protecting the nozzle 110 from dirt, impact, or the like. Incidentally, when the syringe is not a prefilled syringe, the cap 108 may be omitted.

The syringe 100 may be a syringe with an injection needle, a syringe without an injection needle, or the like. For example, when the syringe 100 is a prefilled syringe, the syringe 100 is filled with the liquid medicine 200 in advance, and the liquid medicine 200 is held in a state where the cap 108 is attached. By using the prefilled syringe, the mix-up of medications, contamination of the liquid medicine 200 at a location where the syringe 100 is used, or the like is prevented.

In the syringe 100, it is required that the liquid medicine 200 with which the outer barrel 102 is filled does not leak from the gasket 104 side. In the syringe 100, it is also required that the plunger 106 (namely, the gasket 104) moves (slides) smoothly during use, high flow accuracy is obtained without causing a large disturbance in the discharge of the liquid medicine, and slidability is high, in other words, sliding resistance is low (hereinafter, also referred to as low sliding). Further, in the syringe 100, it is also required that the amount of impurities (for example, insoluble fine particles or the like to be described later) in the liquid medicine 200, which originate from the syringe 100, is small or impurities are not mixed into the liquid medicine 200.

<Gasket>

The gasket 104 that is a sliding member will now be described. FIG. 1(*b*) is a schematic side view showing a configuration of the gasket 104 of the present embodiment. Incidentally, a surface layer 300 to be described later is shown in a cross-sectional view. The gasket 104 includes a base material 104*a*, a tapered portion 104*b*, a body portion 104*c*, and a connecting portion 104*d*. The gasket 104 undergoes an application step to be described later, so that the surface layer 300 shown in FIG. 1(*b*) is formed. Incidentally, in the following description, the surface layer 300 may also be included in the gasket 104 after the application step.

The base material 104*a* is rubber, for example, butyl rubber. Butyl rubber is, for example, a synthetic rubber obtained by copolymerizing isobutylene with a few percent of isoprene by mole ratio. Butyl rubber has good electrical insulation, ozone resistance, weather resistance, aging resistance, and shock absorption. In the present embodiment, since butyl rubber has low gas permeability, does not allow oxygen and the like to permeate therethrough, and is less likely to deteriorate the liquid medicine 200, butyl rubber is used for the base material 104*a* of the gasket 104. In addition, in addition to butyl rubber, natural rubber, styrene butadiene rubber, chloroprene rubber, acrylonitrile rubber, ethylene propylene rubber, urethane rubber, silicone rubber, fluororubber, chlorosulfonated polyethylene rubber, or the like may be used for the base material 104*a*. The rubber used for the base material 104*a* is preferably butyl rubber, isoprene rubber, styrene butadiene rubber, silicone rubber, or the like.

Figure 2:
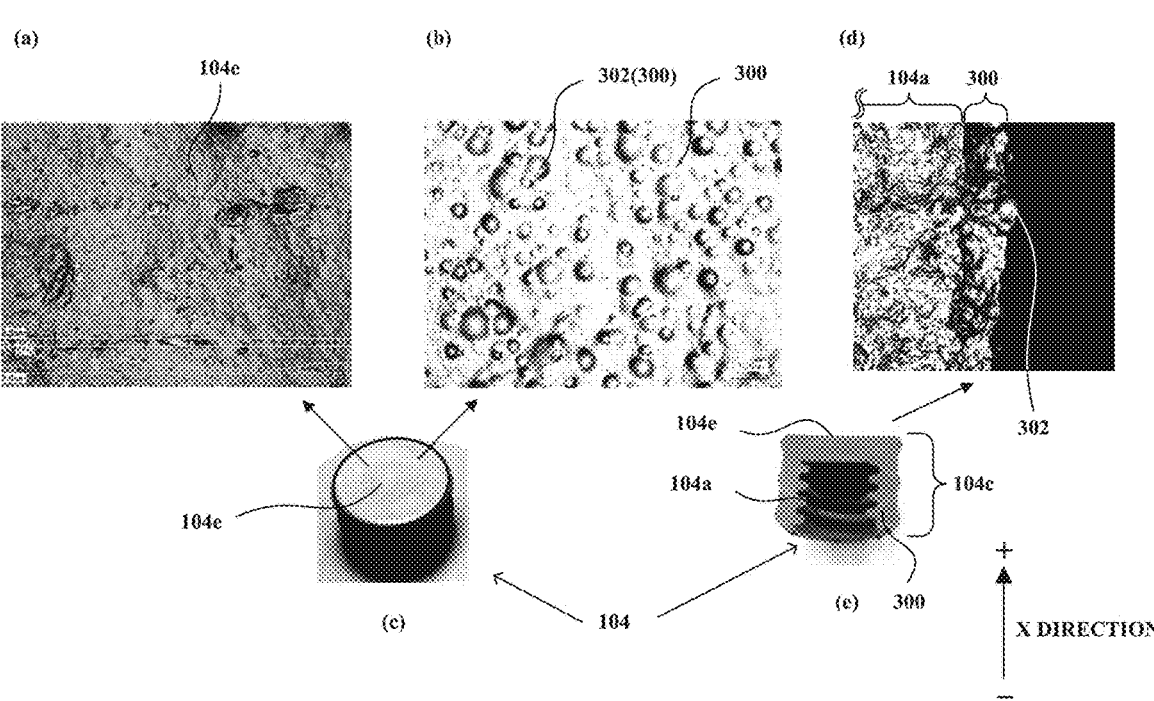
FIG. 2(a) is an enlarged view of the gasket before an application step.
FIG. 2(b) is an enlarged view of a surface layer formed on the gasket after the application step.
FIG. 2(c) is a perspective view showing a planar portion of the gasket.
FIG. 2(d) is an enlarged view of a cross section of the gasket and the surface layer.
FIG. 2(e) is a cross-sectional view of the gasket according to the embodiment.

The tapered portion 104*b* is a portion at the one end (+ side) of the gasket 104 in the X direction, and has a tapered shape. Namely, the tapered portion 104b has a conical shape. Incidentally, the gasket 104 may not include the tapered portion, and a surface of the gasket 104 perpendicular to the X direction may be a flat plane as shown in FIG. 2 to be described later.

The body portion 104c is a side surface of the gasket 104, and includes a plurality of ribs. The plurality of ribs of the body portion 104c come into contact with the inner surface of the outer barrel 102. Incidentally, the body portion 104c may not include a plurality of ribs, and the entire surface of the body portion 104c may be in contact with the inner surface of the outer barrel 102. The connecting portion 104d is a portion on the other end side (− side) of the gasket 104 in the X direction, and is a connecting portion with the plunger 106. A manner in which the connecting portion 104d is connected to the plunger 106 is not particularly limited; however, as described above, the connecting portion 104d may have a shape corresponding to a connecting portion on the plunger 106 side.

The surface layer 300 is formed on the gasket 104 in the application step, and the surface layer 300 enhances sealability to prevent leakage of the liquid medicine 200, and enhances slidability of the plunger 106. In a material forming the surface layer 300, it is also required that insoluble fine particles due to the falling off of the material into the liquid medicine 200 are not generated or the number of insoluble fine particles is small even if generated (hereinafter, also referred to as low insoluble fine particle formation).

<Surface Layer and Coating Liquid>

The material for forming the surface layer 300 (hereinafter, referred to as a coating liquid) is applied to the gasket 104. Incidentally, in addition to the term "application", the term "coating" may be used, and the surface layer 300 may be referred to as a coating film. The surface layer 300 is formed by coating an outer surface of the gasket 104 with the coating liquid.

The coating liquid of the present embodiment contains a flexibility-imparting component and a slidability-imparting component. Here, the flexibility-imparting component is a component that imparts elasticity to the surface layer 300. The surface layer 300 can deform along with the base material 104a due to the flexibility-imparting component when the base material 104a is compressed. The slidability-imparting component is a component that enhances slidability between the gasket 104 and an inner wall of the outer barrel 102. In addition, by using materials having similar compositions for the flexibility-imparting component and the slidability-imparting component, a coating with high compatibility is realized. By increasing the compatibility, the falling off of insoluble fine particles from the surface layer 300 of the gasket 104 into the liquid medicine 200 (hereinafter, referred to as the generation of insoluble fine particles). For example, when a silicon-based material is used as the flexibility-imparting component, a silicon-based material is also used as the slidability-imparting component. In the present embodiment, for example, in the coating liquid, an aqueous silicon-based solution is used as the flexibility-imparting component, and silicon-based rubber particles are used as the slidability-imparting component. Namely, the coating liquid of the present embodiment has a composition in which silicon-based rubber particles are contained in an aqueous silicon-based solution.

The coating liquid is obtained, for example, by adding silicon-based rubber fine particles to a silicon-based solution. The silicon-based solution (silicone-based liquid) may be, for example, a silicone (reactive silicone) having a silanol group and polysiloxane as a basic structure. The silicon-based rubber fine particles may be, for example, silicone rubber having polysiloxane as a basic structure.

The particle size of the silicon-based rubber fine particles is 1 μm or more and 50 μm or less in average particle size. Here, when the particle size of the silicon-based rubber fine particles is less than 1 μm in average particle size, the silicon-based rubber fine particles are likely to aggregate, and the coating liquid is difficult to manufacture, which is a risk. In addition, when the particle size of the silicon-based rubber fine particles is larger than 50 μm in average particle size, the sealing performance decreases, which is a risk.

The gasket 104 is formed through a kneading step of kneading rubber that is a raw material, and a molding step of vulcanizing and molding the kneaded rubber. The surface layer 300 of the gasket 104 is formed by applying the coating liquid through spraying, and then drying the coating liquid, baking the coating liquid thereafter, and cleaning the coating liquid.

<Gasket Manufacturing Method>

A surface coating layer formation method for the gasket 104 (method for manufacturing the gasket 104) according to the present embodiment that realizes low sliding and low insoluble fine particle formation will be described. The surface coating layer formation method of the present embodiment includes an application step, a drying step, a baking step, and a cleaning step. Incidentally, a finishing step of finishing the gasket 104 may be performed before the application step, or may be performed before the cleaning step. In addition, after the cleaning step, a sterilization step of sterilizing the gasket 104 on which the surface layer 300 is formed may be performed.

(Application Step)

In the application step, a predetermined coating thickness of the coating liquid to be applied is, for example, 5 μm. Incidentally, the predetermined coating thickness is not limited to 5 μm, and may be in a range of, for example, 1 μm or more and 50 μm or less, and an appropriate coating thickness depends on the size of the silicon-based rubber fine particles. Here, when the coating thickness is thinner than 1 μm, sliding resistance increases, which is a risk. In addition, when the coating thickness is thicker than 50 μm, there is a high possibility that the sealing performance decreases and the crack of the coating film occurs.

As the coating method, known means such as spin coating, slit coating, dip coating, spray coating, or manual (for example, using a brush) direct coating can be employed; however, in the present embodiment, spray coating is used. Hereinafter, the gasket 104 on which the surface layer 300 is formed through the application step is also referred to simply as the gasket 104.

(Drying Step)

In the drying step, the gasket 104 on which the surface layer 300 is formed by applying the coating liquid is dried at a first temperature, for example, at a temperature of room temperature to 100° C., for a first time period, for example, for 1 hour to 24 hours. Here, when the first temperature is lower than room temperature, it is difficult for the surface layer 300 to dry, and it takes time for drying to be completed, which is a risk. In addition, being lower than room temperature requires a cooled liquid (for example, water), which becomes a burden from the viewpoint of the step. In addition, when the first temperature is high, in the case of a solvent-based coating liquid, there is a safety concern such as fire, and in the case of a water-based coating liquid, the time period required for drying is short, but a smooth surface layer is not formed, which is a risk. In addition, when the first time period is shorter than one hour, drying becomes insufficient, and a smooth surface layer is not formed after baking, which is a risk. Further, when the first time period is longer than 24 hours at a high temperature of 100° C., deterioration of the base material 104a progresses, which is a risk. In addition, an excessively long time period is not preferable from the viewpoint of the step.

(Baking Step)

In the baking step, the gasket after drying is baked at a second temperature, for example, at a temperature of room temperature to 200° C., for a second time period, for example, for 5 minutes to 2 hours. Here, when the second temperature is lower than room temperature, it takes time for the surface layer 300 to cure, which is a risk. In addition, the strength of the formed surface layer 300 decreases, which is a risk. In addition, when the second temperature is higher than 200° C., deterioration of the base material 104a progresses, which is a risk, and there is also a possibility that the surface layer 300 deteriorates. In addition, when the second time period is shorter than 5 minutes, the curing reaction of the surface layer 300 is not completed, which is a risk, and the strength of the surface layer 300 decreases, which is a risk. Further, when the second time period is longer than 2 hours, deterioration of the base material 104a progresses, which is a risk.

FIG. 2(a) is an enlarged view of the gasket 104 before the application step. Incidentally, the gasket 104 shown in FIG. 2 is the gasket 104 that does not have a tapered shape such as the tapered portion 104b, but includes a planar portion 104e (refer to FIG. 2(c)). FIG. 2(b) is an enlarged view of the surface layer 300 formed on the gasket 104 after the application step. FIG. 2(c) is a perspective view showing the planar portion 104e of the gasket 104, and FIGS. 2(a) and 2(b) show the planar portion 104e before and after the application step. It can be found that as shown in FIG. 2(a), the coating liquid is applied to the surface of the gasket 104 made of rubber, as shown in FIG. 2(b), the surface layer 300 is formed on the gasket 104, and silicone rubber particles 302 dispersed in the coating liquid. Incidentally, in FIG. 2(b), only one silicone rubber particle 302 is indicated by a reference sign; however, other round structures in the figure are also the silicone rubber particles 302.

FIG. 2(d) is an enlarged view of a cross section of the base material 104a and the surface layer 300, and is a cross-sectional view of the gasket 104 parallel to the X direction. FIG. 2(e) is a cross-sectional view of the gasket 104, and FIG. 2(d) shows an enlarged portion on the right side of the cross section, in which the surface layer 300 having a predetermined film thickness is formed on the surface of the gasket 104. Incidentally, in FIG. 2(d) as well, only one silicone rubber particle 302 is indicated by a reference sign; however, other round structures in the figure are also the silicone rubber particles 302.

(Cleaning Step)

In the present embodiment, by cleaning the gasket 104 after coating through extraction cleaning, fine particles adhering to the surface layer 300 of the gasket 104 are caused to fall, so that a further reduction in the number of insoluble fine particles is realized.

In the cleaning step, the gasket 104 after baking is subjected to extraction cleaning at a third temperature, for example, at a temperature of room temperature to 200° C., for a third time period, for example, for 5 minutes to 135 minutes. Here, the third temperature lower than room temperature requires a cooled liquid (for example, water), which becomes a burden from the viewpoint of the step. In addition, when the third temperature is higher than 200° C., deterioration of the base material 104a progresses, which is a risk. In addition, when the third time period is shorter than 5 minutes, cleaning becomes insufficient, and the generation of insoluble fine particles cannot be reduced, which is a risk. Further, when the third time period is longer than 135 minutes, deterioration of the base material 104a progresses, which is a risk. In addition, an excessively long time period is not preferable from the viewpoint of the step.

A coating film having, for example, a predetermined thickness of approximately 5 μm to 10 μm is formed on the gasket 104 of the present embodiment by the surface coating layer formation method described above.

<Formulation of Coating Liquid>

Hereinafter, as formulations of the coating liquid, Formulation 1 of the present embodiment and Formulations 2 to 6 of comparative examples will be described. Incidentally, Formulations 1 to 6 correspond to Formulations 1 to 6 of "coating formulations" in the tables of FIGS. 4 to 6 to be described later.

[Formulation 1]

Formulation 1 is a formulation of the coating liquid of the present embodiment, in which a silicon-based material is used as the flexibility-imparting component, and a silicon-based material is also used as the slidability-imparting component. Namely, materials having similar compositions are used for the flexibility-imparting component and the slidability-imparting component.

[Formulation 2]

Formulation 2 is a formulation for comparison with the present embodiment, in which a silicon-based material is used as the flexibility-imparting component, and no slidability-imparting component is included in the formulation. Namely, Formulation 2 is a formulation under conditions where insoluble fine particles originating from the slidability-imparting component are not generated, which can be regarded as a reference for Formulations 1 to 3.

[Formulation 3]

Formulation 3 is a formulation for comparison with the present embodiment, in which a silicon-based material is used as the flexibility-imparting component, and a fluorine-based material is used as the slidability-imparting component. Namely, materials having different (distant) compositions are used for the flexibility-imparting component and the slidability-imparting component.

[Formulation 4]

Formulation 4 is a formulation for comparison with the present embodiment, in which a urethane-based material is used as the flexibility-imparting component, and no slidability-imparting component is included in the formulation. Namely, Formulation 4 is a formulation under conditions where insoluble fine particles originating from the slidability-imparting component are not generated, which can be regarded as a reference for Formulations 4 to 6.

[Formulation 5]

Formulation 5 is a formulation for comparison with the present embodiment, in which a urethane-based material is used as the flexibility-imparting component, and a silicon-based material is used as the slidability-imparting component. Namely, materials having different compositions are used for the flexibility-imparting component and the slidability-imparting component.

[Formulation 6]

Formulation 6 is a formulation for comparison with the present embodiment, in which a urethane-based material is used as the flexibility-imparting component, and a fluorine-based material is used as the slidability-imparting component. Namely, materials having different compositions are used for the flexibility-imparting component and the slidability-imparting component.

<Evaluation 1>

In Evaluation 1, in order to clarify the influence of the formulation of the coating liquid on slidability, leakage, and insoluble fine particles, a sliding resistance measurement, a leakage test, and an insoluble fine particle test were performed using the gaskets 104 on which the surface layers were formed by the coating liquids of Formulations 1 to 6 described above.

In addition, a relationship between the application step and the cleaning step in the surface coating layer formation method of the present embodiment was also evaluated. Specifically, an evaluation was performed by comparing the case of performing the cleaning step and the case of not performing the cleaning step using Formulation 1 in which a silicon-based material was used as the flexibility-imparting component and a silicon-based material was used as the slidability-imparting component and Formulation 3 in which a silicon-based material was used as the flexibility-imparting component and a fluorine-based material was used as the slidability-imparting component.

(Sliding Resistance Measurement)

Figure 3:
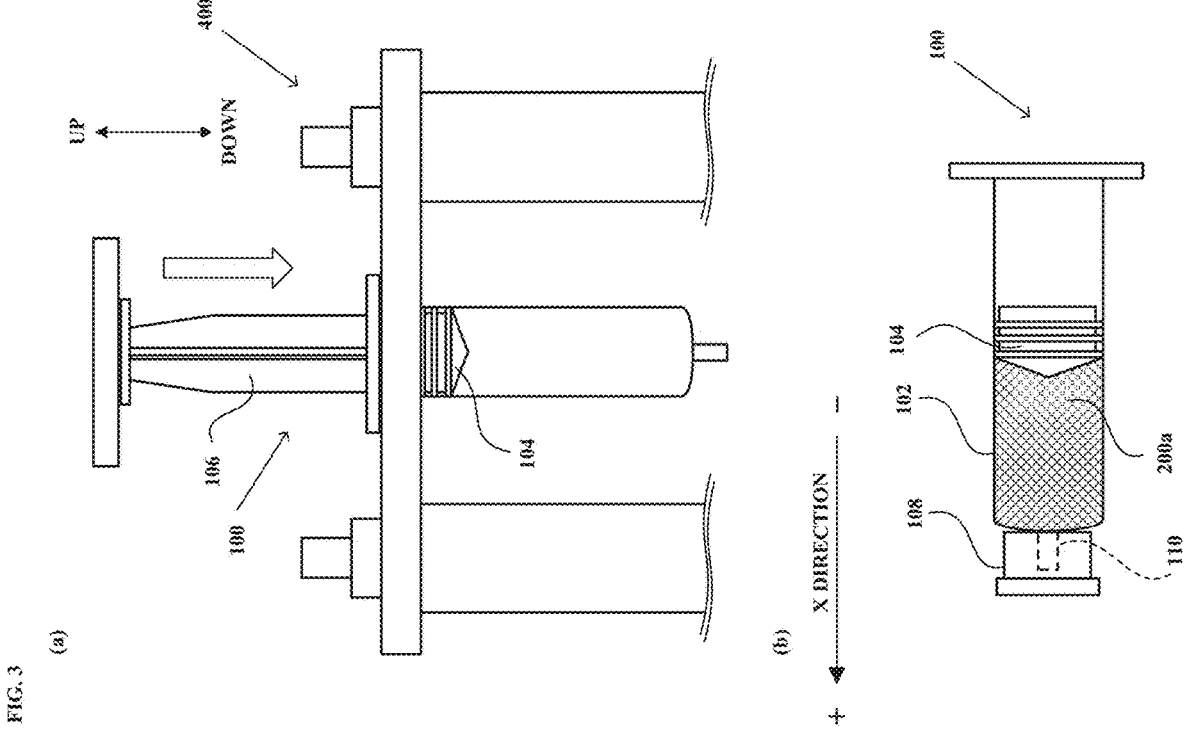
FIG. 3(a) is a front view showing an experiment setup for sliding resistance measurement.
FIG. 3(b) is a top view showing a setup of a leakage test according to the embodiment.

FIG. 3(a) is a front view showing an experiment setup when a sliding resistance measurement is performed, and also shows an up-down direction. As shown in FIG. 3(a), a maximum resistance value (N) was measured (hereinafter, referred to as sliding measurement) when each of the syringes 100 including the gaskets 104 with the surface layers of Study Numbers 1 to 17 to be described later was set in a measuring device 400, the surface layers being formed by applying the coating liquids of Formulations 1 to 6 described above, and then causing the coating liquids to undergo appropriate drying and baking steps, and then causing the coating liquids to undergo cleaning, and the plunger 106 was slid downward (indicated by a white arrow in the figure) from above by a distance of 20 mm (hereinafter, also referred to as a sliding distance) at a speed of 100 mm/min (millimeters per minute) (hereinafter, also referred to as a sliding speed). Incidentally, slidability refers to the ease of sliding, and the unit of a measurement value is "N (Newton)". The larger the value is, the higher sliding resistance is and the more difficult sliding becomes, and the smaller the value is, the lower sliding resistance is and the easier sliding becomes.

(Leakage Test)

FIG. 3(b) is a side view showing a setup of the leakage test, and also shows the X direction corresponding to FIG. 1. Here, each of the gaskets 104 with the surface layers of Study Numbers 1 to 17 to be described later was inserted into the outer barrel 102, the surface layers being formed by applying the coating liquids of Formulations 1 to 6, and then causing the coating liquids to undergo appropriate drying and baking steps, and then causing the coating liquids to undergo cleaning, and the outer barrel 102 was filled with a colored surfactant liquid 200a corresponding to the liquid medicine 200 (dummy liquid medicine) from the nozzle 110 at a tip thereof, and the cap 108 was mounted to seal the nozzle 110. Thereafter, the gaskets 104 were left in an environment at a temperature of 40° C. for 24 hours, and then were transferred to room temperature and were further left for one hour, and in that case, the presence or absence of leakage was checked.

(Insoluble Fine Particle Test)

Each of the gaskets 104 with the surface layers of Study Numbers 1 to 17 to be described later was connected to the plunger 106, the surface layers being formed by applying the coating liquids of Formulations 1 to 6 described above, and then causing the coating liquids to undergo appropriate drying and baking steps, and then causing the coating liquids to undergo cleaning, 2. 25 ml of pure water was poured into the outer barrel 102, the gasket 104 and the plunger 106 were inserted into the outer barrel 102 to seal the outer barrel 102, and the nozzle 110 was further covered and sealed with the cap 108. Accordingly, the pure water was sealed in the syringe 100. After the pure water was sealed in the syringe 100, a sterilization step, for example, an autoclave sterilization process was performed, and then the syringe 100 was mounted on a shaking apparatus and was shaken, and the number of insoluble fine particles in the pure water was measured.

(Results of Evaluation 1)

Figure 4B:
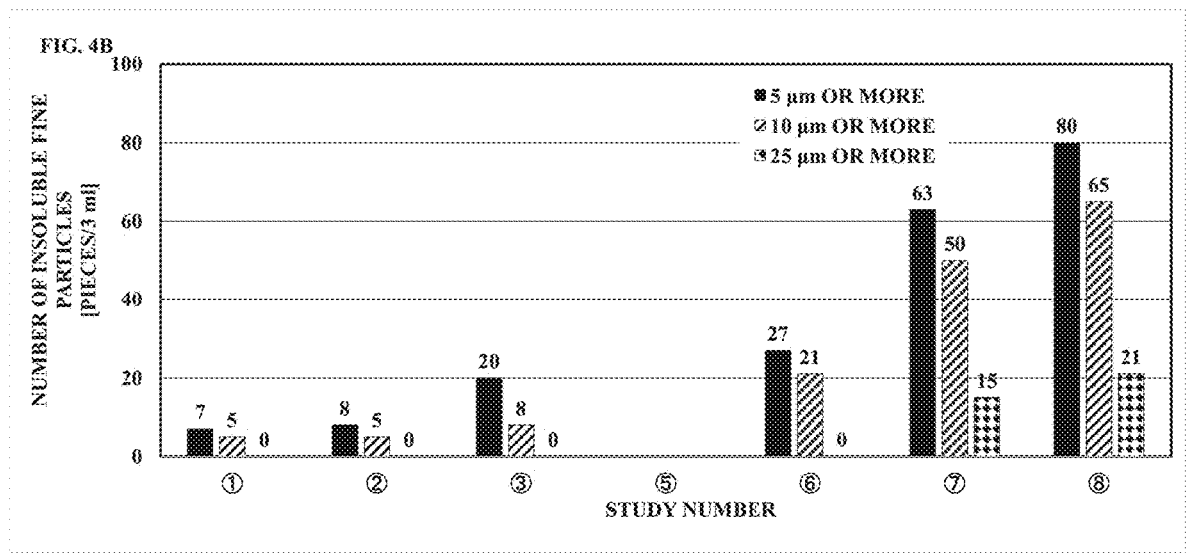
FIG. 4(b) is a graph showing the number of insoluble fine particles in Evaluation 1.

FIG. 4 is a view showing the results of Evaluation 1, FIG. 4(a) is a table showing the results of Evaluation 1, and FIG. 4(b) is a graph showing the number of insoluble fine particles in Evaluation 1. FIG. 4(a) shows sample preparation conditions, coating components, and test contents. The test contents show the results of the sliding resistance value (N) described above, the leakage test (no leakage, –), and the insoluble fine particle test (particles/3 ml). In the row for the sample preparation condition, the study number, the formulation of the coating liquid described above (coating formulation), and the cleaning step are shown. In the row for the coating components, a material used for the flexibility-imparting component (a silicon-based material, a urethane-based material, or the like) and a material used for slidability-imparting component (a silicon-based material, a fluorine-based material, or the like) are shown. The cleaning step is extraction cleaning, particularly high-pressure extraction cleaning, and conditions (temperature×time period) when high-pressure extraction cleaning is performed are also shown. "○" attached to a performed step (or condition) represents that the step (or condition) is adopted. In the row for the insoluble fine particle test, the particle size (5 μm or more, 10 μm or more, or the like) of insoluble fine particles and the number of insoluble fine particles of the particle size (particles/3 ml) are shown. In Evaluation 1, in each case, high-pressure extraction cleaning was performed in the cleaning step, the third temperature was set to 121° C., and the third time period was set to 45 minutes. In addition, circled numbers in the top row of the table represent study numbers, and hereinafter, "Circled Number 1" and the like are referred to as "Study Number 1" and the like. In FIG. 4(b), the horizontal axis indicates the study number, and the vertical axis indicates the number of insoluble fine particles [pieces/3 ml]. In FIG. 4(b), black bars indicate the number of insoluble particles with a particle size of 5 μm or more, diagonal pattern bars indicate the number of insoluble fine particles with a particle size of 10 μm or more, and lattice pattern bars indicate the number of insoluble fine particles with a particle size of 25 μm or more.

In addition, FIG. 4 also shows the results when no cleaning step is performed on both Formulations 1 and 3 (Study Numbers 7 and 8). Incidentally, FIG. 4 also shows columns for the sliding resistance value and the leakage test; however, Study Numbers 7 and 8 are evaluated based on the results of the insoluble fine particle test.

[Study Number 1 (Formulation 1)]

In Formulation 1 using the surface coating layer formation method of the present embodiment, the result was that the sliding resistance value was 3.9 N and there was no leakage. The number of insoluble fine particles with a particle size of 25 μm or more was 0 particles/3 ml, the number of insoluble fine particles with a particle size of 10 μm or more was 5 particles/3 ml, and the number of insoluble fine particles with a particle size of 5 μm or more was 7 particles/3 ml.

[Study Number 2 (Formulation 2)]

In Formulation 2, the result was that the sliding resistance value was 6.0 N and there was no leakage. The number of insoluble fine particles with a particle size of 25 μm or more was 0 particles/3 ml, the number of insoluble fine particles with a particle size of 10 μm or more was 5 particles/3 ml, and the number of insoluble fine particles with a particle size of 5 μm or more was 8 particles/3 ml. Namely, since the result was the same as that of Formulation 1, it was shown that the slidability-imparting component included in Formulation 1 did not increase the number of insoluble fine particles. In addition, even if insoluble fine particles originating from the slidability-imparting component are not generated, it can be said that 8 insoluble fine particles with a particle size of 5 μm or more per 3 ml are mixed in the liquid medicine 200. It is considered that the insoluble fine particles are, for example, insoluble fine particles originating from dust suspended in the air, or particles that originally adhere to the container and that cannot be removed in the cleaning step.

[Study Number 3 (Formulation 3)]

In Formulation 3, the result was that the sliding resistance value was 5.8 N and there was no leakage. The number of insoluble fine particles with a particle size of 25 μm or more was 0 particles/3 ml, the number of insoluble fine particles with a particle size of 10 μm or more was 8 particles/3 ml, and the number of insoluble fine particles with a particle size of 5 μm or more was 20 particles/3 ml. Namely, it was shown that even if the same silicon-based material was used for the flexibility-imparting component, when a fluorine-based material was used for the slidability-imparting component, a larger number of insoluble fine particles with a particle size of 5 μm or more were generated than in Formulation 1.

[Study Number 5 (Formulation 5)]

In Formulation 5, since the slidability-imparting component was not mixed with the flexibility-imparting component, a surface layer could not be formed (was indispersible, and the same applies below). For this reason, three evaluation results could not be obtained.

[Study Number 6 (Formulation 6)]

In Formulation 6, the sliding resistance value was 21.1 N. The number of insoluble fine particles with a particle size of 25 μm or more was 0 particles/3 ml, the number of insoluble fine particles with a particle size of 10 μm or more was 21 particles/3 ml, and the number of insoluble fine particles with a particle size of 5 μm or more was 27 particles/3 ml. In Formulation 6, the sliding resistance value was also high, and a large number of insoluble fine particles were also observed.

[Study Number 7 (Formulation 1)]

In Study Number 7, Formulation 1 using the surface coating layer formation method of the present embodiment was used, but high-pressure extraction cleaning was not performed. In Study Number 7, the number of insoluble fine particles with a particle size of 25 μm or more was 15 particles/3 ml, the number of insoluble fine particles with a particle size of 10 μm or more was 50 particles/3 ml, and the number of insoluble fine particles with a particle size of 5 μm or more was 63 particles/3 ml.

[Study Number 8 (Formulation 3)]

In Study Number 8, Formulation 3 was used, but high-pressure extraction cleaning was not performed. In Study Number 8, the number of insoluble fine particles with a particle size of 25 μm or more was 21 particles/3 ml, the number of insoluble fine particles with a particle size of 10 μm or more was 65 particles/3 ml, and the number of insoluble fine particles with a particle size of 5 μm or more was 80 particles/3 ml.

From the above results, it could be found that when a surface layer was formed on the gasket 104 using the surface coating layer formation method of the present embodiment, sliding resistance was low, there was also no leakage, and the generation of insoluble fine particles could also be reduced.

In addition, in both Formulation 1 and Formulation 3, when the cleaning step was not performed, a large number of insoluble fine particles were observed. However, it was shown that the generation of insoluble fine particles was suppressed in Formulation 1 compared to Formulation 3.

Meanwhile, when Study Number 1 (Formulation 1) and Study Number 7 (Formulation 1) in FIG. 4 described above are compared to each other, and Study Number 3 (Formulation 3) and Study Number 8 (Formulation 3) in FIG. 4 are compared to each other, in both cases, the number of insoluble fine particles can be reduced by performing the cleaning step. However, it was found that the degree of reduction in the number of insoluble fine particles was larger in Formulation 1 using the surface coating layer formation method of the present embodiment compared to Formulation 3. Namely, the degree of reduction in the number of insoluble fine particles for Study Number 1 with respect to that for Study Number 7 (89% reduction) was greater than the degree of reduction in the number of insoluble fine particles for Study Number 3 with respect to that for Study Number 8 (70% reduction).

As described above, from Evaluation 1, by forming the surface layer 300 on the gasket 104 using the surface coating layer formation method of the present embodiment including the application step using a silicon-based material for the flexibility-imparting component and also using silicon-based material having a similar composition for the slidability-imparting component, and the cleaning step, both low sliding resistance and low insoluble fine particle formation could be achieved.

<Evaluation 2>

Figure 5B:
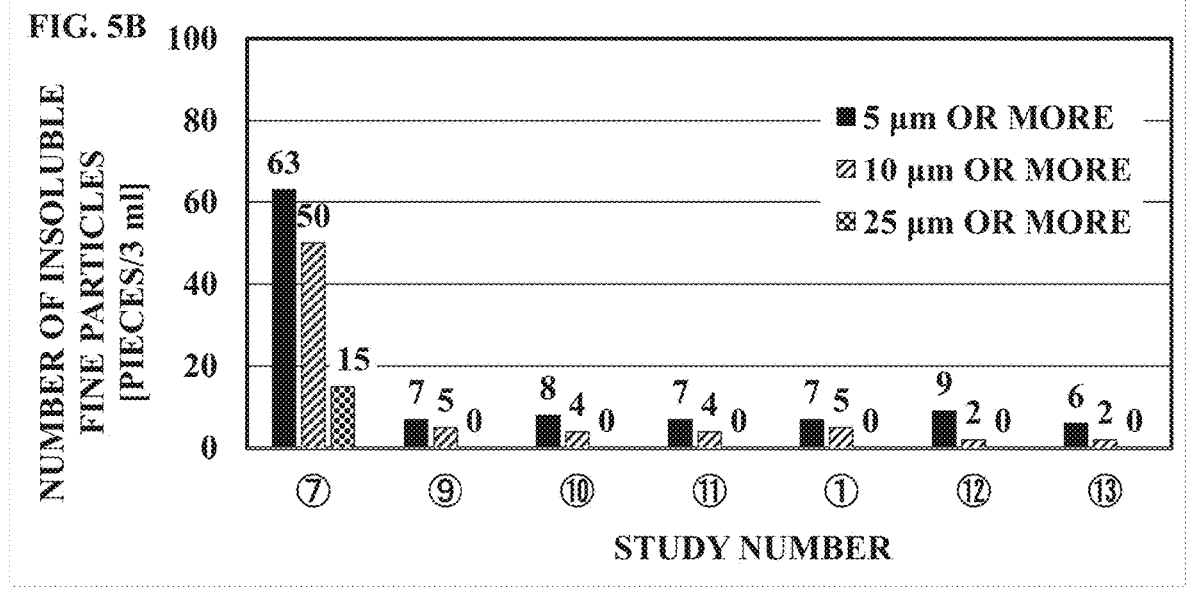
FIG. 5(b) is a graph showing the number of insoluble fine particles in Evaluation 2.

FIG. 5 is a view showing the results of Evaluation 2, FIG. 5(*a*) is a table showing the results of Evaluation 2, and FIG. 5(*b*) is a graph showing the number of insoluble fine particles in Evaluation 2. FIG. 5(*a*) shows sample preparation conditions, coating components, and test contents. The test contents show the results of the insoluble fine particle test (pieces/3 ml). In the row for the sample preparation condition, the study number, the coating formulation, and the cleaning step (extraction or high-pressure extraction) are shown. In the row for the coating components, a material used for the flexibility-imparting component (a silicon-based material, a urethane-based material, or the like) and a material used for slidability-imparting component (a silicon-based material, a fluorine-based material, or the like) are shown. In the row for the cleaning step (extraction or high-pressure extraction), conditions (temperature×time period) when cleaning is performed are also shown. "○" attached to a performed step (or condition) represents that the step (or condition) is adopted. In the row for the insoluble fine particle test, the particle size (5 μm or more, 10 μm or more, or the like) of insoluble fine particles and the number of insoluble fine particles of the particle size (particles/3 ml) are shown. The conditions of the cleaning step when the surface layer 300 was formed on the gasket 104 using the surface coating layer formation method of the present embodiment were evaluated. FIG. 5(*a*) is a table showing the results when the cleaning step is performed on the surface layer 300 of Formulation 1 while changing temperature and time period, and FIG. 5(*b*) is a graph based on the table of FIG. 5(*a*). Incidentally, Evaluation 2 is evaluated based on the results of the insoluble fine particle test. In addition, as the cleaning step, extraction cleaning and high-pressure extraction cleaning were performed.

(Study Number 7)

This study number is the result of Study Number 7 in FIG. 4, and description will be omitted.

(Study Number 9 (when Extraction Cleaning was Performed at a Temperature of 60° C. for 45 Minutes))

The number of insoluble fine particles with a particle size of 25 μm or more was 0 particles/3 ml, the number of insoluble fine particles with a particle size of 10 μm or more was 5 particles/3 ml, and the number of insoluble fine particles with a particle size of 5 μm or more was 7 particles/3 ml.

(Study Number 10 (when Extraction Cleaning was Performed at a Temperature of 80° C. for 45 Minutes))

The number of insoluble fine particles with a particle size of 25 μm or more was 0 particles/3 ml, the number of insoluble fine particles with a particle size of 10 μm or more was 4 particles/3 ml, and the number of insoluble fine particles with a particle size of 5 μm or more was 8 particles/3 ml.

(Study Number 11 (when High-Pressure Extraction Cleaning was Performed at a Temperature of 121° C. for 5 Minutes))

The number of insoluble fine particles with a particle size of 25 μm or more was 0 particles/3 ml, the number of insoluble fine particles with a particle size of 10 μm or more was 4 particles/3 ml, and the number of insoluble fine particles with a particle size of 5 μm or more was 7 particles/3 ml.

(Study Number 1 (when High-Pressure Extraction Cleaning was Performed at a Temperature of 121° C. for 45 Minutes))

This study number is the result of Study Number 1 (Formulation 1) of Evaluation 1 in FIG. 4, and description will be omitted.

(Study Number 12 (when High-Pressure Extraction Cleaning was Performed at a Temperature of 121° C. for 90 Minutes))

The number of insoluble fine particles with a particle size of 25 μm or more was 0 particles/3 ml, the number of insoluble fine particles with a particle size of 10 μm or more was 2 particles/3 ml, and the number of insoluble fine particles with a particle size of 5 μm or more was 9 particles/3 ml.

(Study Number 13 (when High-Pressure Extraction Cleaning was Performed at a Temperature of 170° C. for 45 Minutes))

The number of insoluble fine particles with a particle size of 25 μm or more was 0 particles/3 ml, the number of insoluble fine particles with a particle size of 10 μm or more was 2 particles/3 ml, and the number of insoluble fine particles with a particle size of 5 μm or more was 6 particles/3 ml.

From the above results, compared to Study Number 7 in which the cleaning step was not performed, good results were obtained for all Study Numbers 9 to 13 in which the cleaning step was performed.

<Evaluation 3>

Figure 6B:
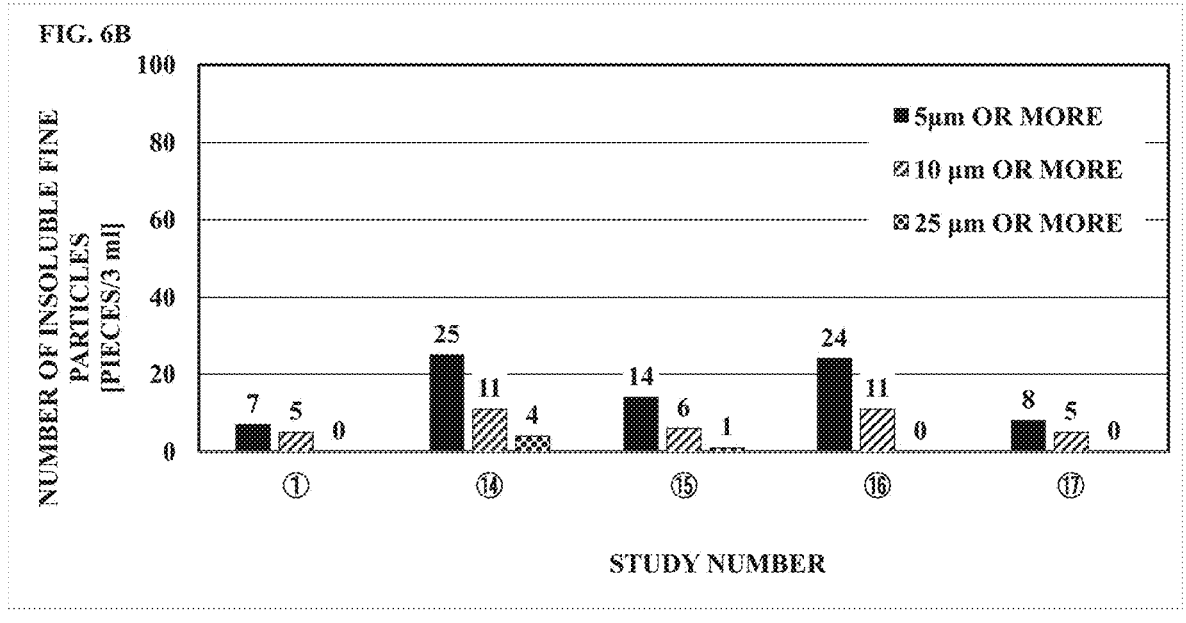
FIG. 6 is a view showing the results of Evaluation 3 of the embodiment, FIG. 6(*a*) is a table showing the results of Evaluation 3, and FIG. 6(*b*) is a graph showing the number of insoluble fine particles in Evaluation 3.

FIG. 6 is a view showing the results of Evaluation 3, FIG. 6(*a*) is a table showing the results of Evaluation 3, and FIG. 6(*b*) is a graph showing the number of insoluble fine particles in Evaluation 3. Incidentally, FIG. 6 is a table and a graph similar to FIG. 4. Regarding the cleaning step of the surface coating layer formation method of the present embodiment, the case of using a shaking apparatus, the case of using ultrasonic cleaning, and the case of using a shaker for the surface layer 300 of Formulation 1 were evaluated, and were compared to the case of using high-pressure extraction cleaning of Study Number 1 (Evaluation 1). FIG. 6(*a*) is a table showing the results when the various cleaning steps described above are performed on the surface layer 300 of Formulation 1, and FIG. 6(*b*) is a graph based on the table of FIG. 6(*a*).

(Study Number 1 (when High-Pressure Extraction Cleaning was Used))

This study number is the result of Study Number 1 (Formulation 1) of Evaluation 1 in FIG. 4, and description will be omitted.

(Study Number 14 (when Shaking Apparatus was Used))

When a shaking apparatus was used in the cleaning step, the result was that the sliding resistance value was 4.4 N and there was no leakage. The number of insoluble fine particles with a particle size of 25 μm or more was 4 particles/3 ml, the number of insoluble fine particles with a particle size of 10 μm or more was 11 particles/3 ml, and the number of insoluble fine particles with a particle size of 5 μm or more was 25 particles/3 ml. When a shaking apparatus was used, a large number of insoluble fine particles with a particle size of 25 μm or more were observed.

(Study Number 15 (when Ultrasonic Cleaning was Used))

When ultrasonic cleaning was used in the cleaning step, the result was that the sliding resistance value was 4.8 N and there was no leakage. The number of insoluble fine particles with a particle size of 25 μm or more was 1 particle/3 ml, the number of insoluble fine particles with a particle size of 10 μm or more was 6 particles/3 ml, and the number of insoluble fine particles with a particle size of 5 μm or more was 14 particles/3 ml. When ultrasonic cleaning was used, insoluble fine particles with a particle size of 25 μm or more were observed.

(Study Number 16 (when Orbital Shaker was Used))

When a shaker was used in the cleaning step, the result was that the sliding resistance value was 4.2 N and there was no leakage. The number of insoluble fine particles with a particle size of 25 μm or more was 0 particle/3 ml, the number of insoluble fine particles with a particle size of 10 μm or more was 11 particles/3 ml, and the number of insoluble fine particles with a particle size of 5 μm or more was 24 particles/3 ml. When a shaker was used, a large number of insoluble fine particles with a particle size of 5 μm or more were observed.

(Study Number 17 (when Ultrasonic Cleaning was Used after High-Pressure Extraction Cleaning))

When ultrasonic cleaning was also used after high-pressure extraction cleaning in the cleaning step, the result was that the sliding resistance value was 3.7 N and there was no leakage. The number of insoluble fine particles with a particle size of 25 μm or more was 0 particles/3 ml, the number of insoluble fine particles with a particle size of 10 μm or more was 5 particles/3 ml, and the number of insoluble fine particles with a particle size of 5 μm or more was 8 particles/3 ml. Even if ultrasonic cleaning was used after high-pressure extraction cleaning, no large difference was observed compared to when only high-pressure extraction cleaning was performed.

From the above results, it was found to be preferable that high-pressure extraction cleaning was performed in the cleaning step on the gasket 104 on which the surface layer

300 was formed by Formulation 1. In addition, it was found that insoluble fine particles could be sufficiently removed only by high-pressure extraction cleaning without employing a combination of the high-pressure extraction cleaning and other cleaning methods.

SUMMARY

Study Number 1 of the present embodiment to Study Numbers 2, 3, and 5 to 17 that are comparative examples, which have been described using FIGS. 4 to 6, will be summarized below.

In Study Number 1, the sliding resistance value could be reduced to approximately $\frac{1}{20}$ to $\frac{2}{3}$ compared to Study Numbers 2, 3, and 6.

In Study Number 1, the number of insoluble fine particles could be as low as that in Study Number 2, and the number of insoluble fine particles could be reduced to approximately $\frac{1}{2}$ to $\frac{1}{7}$ compared to Study Numbers 3 and 6 . . . .

From the results of Study Numbers 1 and 9 to 17, the number of insoluble fine particles could be reduced by using high-pressure extraction cleaning in the cleaning step, and setting the temperature to 60° C. or higher.

When Study Number 1 and Study Number 17 were compared to each other, even if ultrasonic cleaning was performed after high-pressure extraction cleaning was performed, no change was observed in the number of insoluble fine particles.

From a comparison between Study Number 7 and Study Number 8, the number of insoluble fine particles in Study Number 8 was approximately 1.3 times higher than that in Study Number 7.

From a comparison between Study Number 1 and Study Number 7, it was confirmed that the number of insoluble fine particles was reduced by approximately $\frac{1}{9}$ to $\frac{1}{10}$ by high-pressure extraction cleaning. Meanwhile, in a comparison between Study Number 3 and Study Number 8, the effect of a reduction in the number of insoluble fine particles by high-pressure extraction cleaning was approximately $\frac{1}{4}$ to $\frac{1}{7}$.

As described above, according to the present embodiment, it is possible to provide the surface coating layer formation method and the gasket manufacturing method capable of reducing the falling off of insoluble fine particles into the liquid medicine while preventing leakage of the liquid medicine and maintaining stable slidability.

The preferred embodiment of the present invention has been described above; however, the present invention is not limited thereto, and various modifications or changes can be made without departing from the concept of the present invention.

In addition, for example, embodiments of the present invention include the following concepts.

[Concept 1]

A surface coating layer formation method of at least one embodiment of the present invention is a surface coating layer formation method by which a surface coating layer for improving slidability is formed on a surface of a sliding member using rubber as a base material, a material of the surface coating layer having a composition in which silicon-based rubber particles are contained in a silicon-based solution, the method including: an application step of applying the material to a surface of the base material so as to have a predetermined coating thickness; a drying step of drying the sliding member after the application at a first temperature for a first time period; a baking step of baking the sliding member after the drying at a second temperature for a second time period; and a cleaning step of extraction-cleaning the sliding member after the baking at a third temperature for a third time period.

[Concept 2]

A particle size of the silicon-based rubber particles may be 1 μm or more and 50 μm or less in average particle size.

[Concept 3]

The predetermined coating thickness may be 1 μm or more and 50 μm or less.

[Concept 4]

The third temperature may be room temperature or higher and 200° C. or lower, and the third time period may be 5 minutes or more and 135 minutes or less.

[Concept 5]

A surface coating layer formation method of at least one embodiment of the present invention is a surface coating layer formation method by which a surface coating layer for improving slidability is formed on a surface of a gasket that is disposed at a tip portion of a plunger used in a syringe and that slides against an inner barrel wall of the syringe, a material of the surface coating layer having a composition in which silicon-based rubber particles are contained in a silicon-based solution, the method including: an application step of applying the material to the surface of the gasket so as to have a predetermined coating thickness; a drying step of drying the gasket after the application at a first temperature for a first time period; a baking step of baking the gasket after the drying at a second temperature for a second time period; and a cleaning step of extraction-cleaning the gasket after the baking at a third temperature for a third time period.

[Concept 6]

A gasket manufacturing method of at least one embodiment the present invention is a gasket manufacturing method by which a gasket that is disposed at a tip portion of a plunger used in a syringe and that slides against an inner barrel wall of the syringe, the gasket including a surface coating layer for improving slidability on a surface of a rubber base material, a material of the surface coating layer having a composition in which silicon-based rubber particles are contained in a silicon-based solution, the method including: an application step of applying the material to a surface of the base material so as to have a predetermined coating thickness; a drying step of drying the gasket after the application at a first temperature for a first time period; a baking step of baking the gasket after the drying at a second temperature for a second time period; and a cleaning step of extraction-cleaning the gasket after the baking at a third temperature for a third time period.

REFERENCE SIGNS LIST

100: syringe
102: outer barrel
104: gasket
104*a*: base material
104*b*: tapered portion
104*c*: body portion
104*d*: connecting portion
104*e*: planar portion
106: plunger
106*a*: flange
108: cap
110: nozzle
200: liquid medicine
200*a*: surfactant liquid
300: surface layer

17

302: silicone rubber particle
400: measuring device

The invention claimed is:

1. A surface coating layer formation method by which a surface coating layer for improving slidability is formed on a surface of a sliding member using rubber as a base material, a material of the surface coating layer having a composition in which silicon-based rubber particles are contained in a silicon-based solution, the method comprising:

an application step of applying the material to a surface of the base material so as to have a predetermined coating thickness;

a drying step of drying the sliding member after the application at a first temperature for a first time period;

a baking step of baking the sliding member after the drying at a second temperature for a second time period; and a cleaning step of extraction-cleaning the sliding member after the baking at a third temperature for a third time period.

2. The surface coating layer formation method according to claim 1, wherein a particle size of the silicon-based rubber particles is 1 μm or more and 50 μm or less in average particle size.

3. The surface coating layer formation method according to claim 2, wherein the predetermined coating thickness is 1 μm or more and 50 μm or less.

4. The surface coating layer formation method according to claim 2, wherein the third temperature is room temperature or higher and 200° C. or lower, and the third time period is 5 minutes or more and 135 minutes or less.

5. The surface coating layer formation method according to claim 1, wherein the predetermined coating thickness is 1 μm or more and 50 μm or less.

6. The surface coating layer formation method according to claim 1, wherein the third temperature is room temperature or higher and 200° C. or lower, and the third time period is 5 minutes or more and 135 minutes or less.

7. A surface coating layer formation method by which a surface coating layer for improving slidability is formed on a surface of a gasket that is disposed at a tip portion of a plunger used in a syringe and that slides against an inner barrel wall of the syringe, a material of the surface coating layer having a composition in which silicon-based rubber particles are contained in a silicon-based solution, the method comprising:

an application step of applying the material to the surface of the gasket so as to have a predetermined coating thickness;

a drying step of drying the gasket after the application at a first temperature for a first time period;

a baking step of baking the gasket after the drying at a second temperature for a second time period; and a cleaning step of extraction-cleaning the gasket after the baking at a third temperature for a third time period.

8. A gasket manufacturing method by which a gasket that is disposed at a tip portion of a plunger used in a syringe and that slides against an inner barrel wall of the syringe, the gasket including a surface coating layer for improving slidability on a surface of a rubber base material, a material of the surface coating layer having a composition in which silicon-based rubber particles are contained in a silicon-based solution, the method comprising:

an application step of applying the material to a surface of the base material so as to have a predetermined coating thickness;

a drying step of drying the gasket after the application at a first temperature for a first time period;

a baking step of baking the gasket after the drying at a second temperature for a second time period; and a cleaning step of extraction-cleaning the gasket after the baking at a third temperature for a third time period.

* * * * *